United States Patent [19]

Le Coent

[11] Patent Number: 5,690,880
[45] Date of Patent: Nov. 25, 1997

[54] PROCESS FOR THE PRODUCTION OF PLASTIC MATERIAL PARTS BY CONTROLLED MOLDING-THERMOFORMING

[76] Inventor: Fernand Le Coent, 1 Avenue des Lilas, 44470 Thouare sur Loire, France

[21] Appl. No.: 392,891

[22] PCT Filed: Mar. 9, 1993

[86] PCT No.: PCT/FR93/00844

§ 371 Date: Mar. 1, 1995

§ 102(e) Date: Mar. 1, 1995

[87] PCT Pub. No.: WO94/05481

PCT Pub. Date: Mar. 17, 1994

[30] Foreign Application Priority Data

Sep. 3, 1992 [FR] France ................. 92 10658

[51] Int. Cl.$^6$ ............. B29C 51/02; B29C 51/12
[52] U.S. Cl. ............. 264/257; 264/266; 264/322; 264/325
[58] Field of Search ............. 264/163, 257, 264/258, 266, 294, 320, 325, 327, 259, 319, 322, 108

[56] References Cited

U.S. PATENT DOCUMENTS

| | | | |
|---|---|---|---|
| 3,763,548 | 10/1973 | Anderson | 264/266 |
| 3,781,969 | 1/1974 | Anderson | 264/266 |
| 4,179,485 | 12/1979 | Tritten | 264/60 |
| 4,357,381 | 11/1982 | Wilson | 264/327 |
| 4,459,092 | 7/1984 | Hatakeyama | 425/112 |
| 4,547,910 | 10/1985 | Roberts et al. | 264/129 |
| 4,784,814 | 11/1988 | Diethelm et al. | 264/102 |
| 5,037,928 | 8/1991 | Li et al. | 264/126 |
| 5,082,436 | 1/1992 | Choi et al. | 264/327 |
| 5,154,872 | 10/1992 | Masui et al. | 264/266 |
| 5,178,708 | 1/1993 | Hara et al. | 264/257 |
| 5,352,397 | 10/1994 | Hara et al. | 264/266 |
| 5,354,397 | 10/1994 | Miyake et al. | 264/266 |

FOREIGN PATENT DOCUMENTS

| | | |
|---|---|---|
| 0 041 004 | 12/1981 | European Pat. Off. . |
| 0 196 946 | 10/1986 | European Pat. Off. . |
| 0 331 447 | 9/1989 | European Pat. Off. . |
| 2 602 454 | 2/1988 | France . |
| 833 118 | 7/1949 | Germany . |

Primary Examiner—Angela Y. Ortiz
Attorney, Agent, or Firm—Young & Thompson

[57] ABSTRACT

A process for the production of a plastic material part with a wear-resistant surface, having a predetermined nonplanar shape, comprising heating a blank of plastic material on a first side thereof opposite a second side on which it is desired to produce the wear-resistant surface, to adjacent the melting temperature of the plastic material, such that the temperature of the second side is substantially lower than the temperature of the first side. The blank thus heated on only the first side is introduced into a mold cavity, and is subjected to elevated pressure in the mold cavity with a surface of the mold cavity in contact with the second surface of the blank having a nonplanar shape complementary to the desired predetermined nonplanar shape of the second surface, thereby to impart to the second surface that predetermined shape while the second surface is at that substantially lower temperature. The surface of the mold cavity is produced either by extending a punch into the mold cavity in contact with the blank, or else the surface of the mold cavity is stationary and the blank is pressed into contact with the stationary surface of the mold cavity by pressure of a liquid, or both. The blank is of high molecular weight polyethylene having molecular chains oriented parallel to the second surface at least adjacent the second surface. The formed blank is for example an osteo implant such as a cotyle.

9 Claims, 2 Drawing Sheets

PROCESS FOR THE PRODUCTION OF PLASTIC MATERIAL PARTS BY CONTROLLED MOLDING-THERMOFORMING

The present invention relates to a process for the production by controlled molding-thermoforming of parts of plastic material resistent to friction and to flow.

A certain number of plastic material parts such as prosthetic joints or mechanical parts such as pinion, guide plate, roller, bearing, and screw, etc. have a limited lifetime because of the phenomena of material flow and wear connected with friction arising during use of said parts. This problem is particularly crucial in the case of orthopaedic implants, principally hip and knee prostheses which are made of metal with the interposition of a wear member. High molecular weight polyethylene (HMWPE) is particularly used for this production. However, this material, although having exceptional friction and anti-wear properties, cannot be used in conventional techniques applied to polymers, such as injection. This is why most of the implants are produced by machining. Unfortunately, these machined productions have the great drawback of not having an excellent surface, as they have machining ridges. Moreover, the poor coefficient and roughness (Ra) give rise to wear debris which the body throws off by the generation of macrophages which give rise to enzymes. These latter then attack the prosthesis by dissolving in particular the sealing materials, thereby giving rise to destruction of the connection of this latter and requiring a new surgical intervention.

As a result, to improve the mechanical properties of these parts subjected to large mechanical stresses, there has already been proposed a certain number of solutions. There is thus known, from FR-A-2.578.780, a process which permits producing plastic material parts by forging, orienting the chains of molecules of said used material, which is generally a high molecular weight material, and thus improving significantly the mechanical properties of said parts, particularly the resistance to flow. However, the process described in this patent does not permit improving substantially the resistance to flow, to wear and the obtention of elastic memory of the homogeneous material guaranteeing dimensional stability. The lack of resistance to wear and flow therefore does not permit increasing substantially the lifetime of the implants by this process.

A process for the production of parts of plastic material by controlled molding-thermoforming is also described in U.S. Pat. No. 4,459,092. This patent comprises the introduction into a mold cavity of a blank of plastic material P1 and of a plastic material P2 at a temperature near or equal to the melting temperature of P2, the part being formed in the mold by means of a punch movable in said cavity and by the injection pressure of the plastic material P2. The blank P1 is subjected to no thermal treatment.

The object of the present invention is therefore to provide a process for the production of parts such as prosthetic articulations, various mechanical parts, etc., having substantially improved mechanical properties particularly as to resistance to flow, to tension, to wear and to fatigue without having substantial shrinkage during production.

The present invention thus relates to a process for the production of plastic material parts by controlled molding-thermoforming, characterized in that there is introduced into the interior of a mold cavity at least one blank P1 of plastic material first heated so as to have different temperature regions, forming the part in the mold by means of a punch movable in said mold cavity and/or by the injection pressure of a plastic material P2 introduced into said cavity at a temperature near or equal to the melting temperature.

According to a preferred embodiment of the invention, the plastic material P2 which has a molecular weight equal to or less than P1 is introduced by injection and the punch is displaced so that it comes preferably into contact with the blank of material thereby causing the blank and the injected plastic material to match the shape of the closed matrix constituted by the walls of the mold cavity forming the imprint of the cavity and of the punch. Because of this, the blank, which is constituted of a polymeric material, has molecular chains oriented parallel to the friction surface at least in the region of the part located below or flush with this surface.

A device permitting the practice of the above process, comprises a mold delimiting a cavity of two parts, complementary to the profile of the final part to be obtained, said mold comprising at least one injection point permitting the introduction of an injectable plastic material and/or a movable punch into the cavity and closing said mold cavity.

This device and this process are more particularly adapted for the production of orthopaedic prostheses or implants and various mechanical parts.

Other characteristics and advantages of the invention will become apparent from a reading of the description which follows and the accompanying drawings, which description and drawings are given only by way of example. In these drawings.

According to the invention, the practice of the process permitting the production of plastic material parts which have high resistance to wear, to flow and to fatigue, requires placing in a mold and producing a blank 4 of plastic material P1. The mold is generally an open mold in two parts. This mold is generally provided with an injection nozzle and its mold cavity 1 can be closed by a movable punch 3. This blank 4, to permit producing optimum mechanical properties of the final part, will preferably be constituted by a crystalline or semi-crystalline non-injectable thermoplastic material such for example as a high molecular weight plastic material. There can be mentioned by way of example very high molecular weight polyethylene which is frequently used particularly for the production of prosthetic articulations and friction parts. This blank can also be reinforced by means of a woven or non-woven reinforcement such as a load of glass fibers for example. This heated blank has different temperature regions, at least one of the regions being at a temperature near or equal to the melting temperature of the material P1 that is used. By a near temperature, is meant a temperature higher or lower than the melting temperature of the material. For example, for polyethylene, there is chosen a temperature comprised in the range from 20° C. below the melting temperature MT of the polyethylene to 10° C. above this melting temperature MT, or more. It is to be noted that the melting temperature MT of polyethylene is determined by calorimetry and that it corresponds to the maximum of the speed of transformation registered during calorimetry. This blank could also be heated on only one surface which would be the forward surface adhering to the plastic material P2 which is injected or compressed. In this case it is a matter of superficial or surface heating. This heating is always performed prior to introduction of the blank into the mold.

Figure 5:
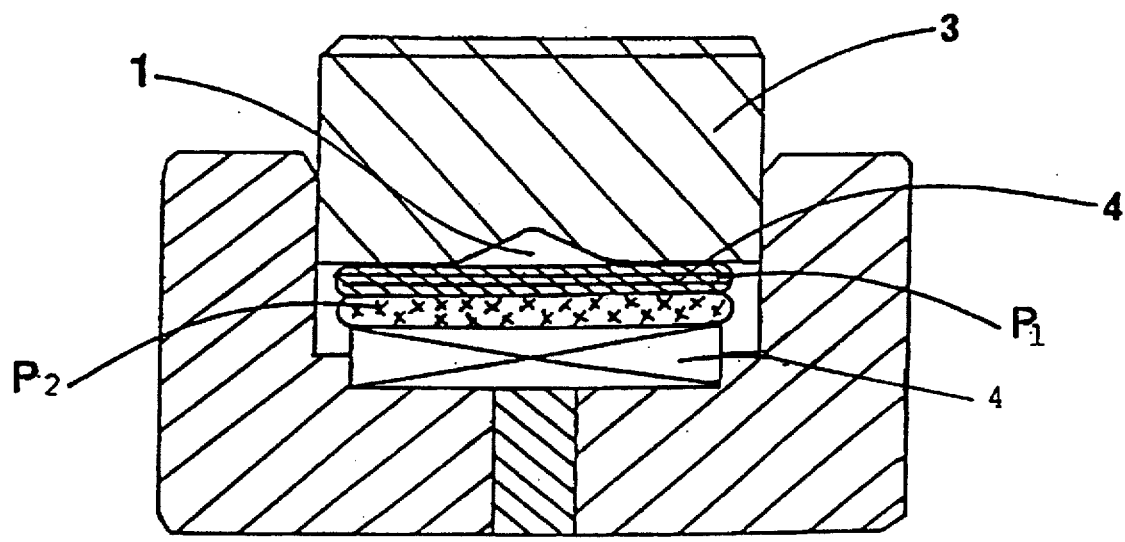
FIG. 5 is a cross-sectional view of a mold provided with a movable punch before compression and in which the cavity is filled by two blanks and a layered reinforced layer.

In addition to this blank 4, there can be introduced within the mold cavity a plastic material P2 brought to a temperature equal or near to the melting temperature, this plastic material being preferably injectable. This plastic material P2 has a molecular weight lower than that of material P1. This plastic material P2 can be injected within the mold cavity in a large number of ways which are functions of the configuration of the mold and of the number of blanks introduced. The different ways of production will be described hereinafter. It could also be provided that the plastic material P2 not be, as is frequently the case for plastic material P1, injectable. In this case, there are available layered plastic materials P1 and P2 in the respective forms of a blank and a plug within the mold cavity, then the assembly is compressed to form the part. This embodiment is shown in FIG. 5.

Figure 1:
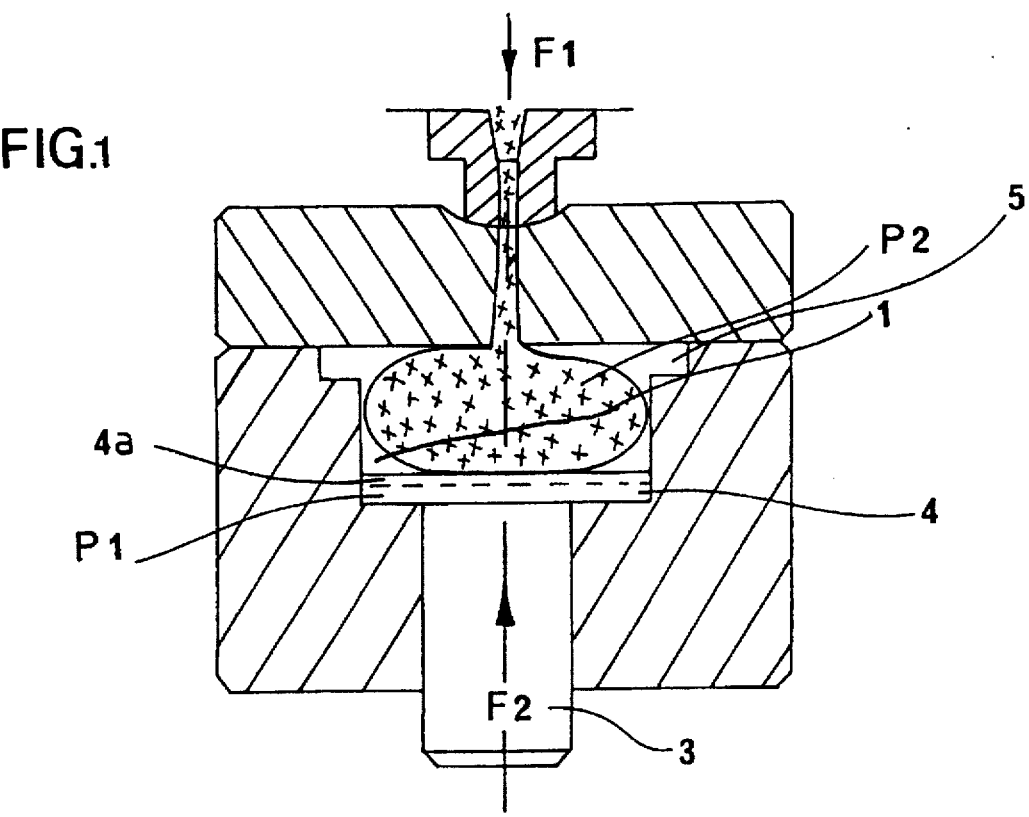
FIG. 1 is a cross-sectional view of a mold provided with a movable punch and an injection nozzle permitting the practice of the process of the invention, said mold enclosing in its mold cavity a blank.
Figure 2:
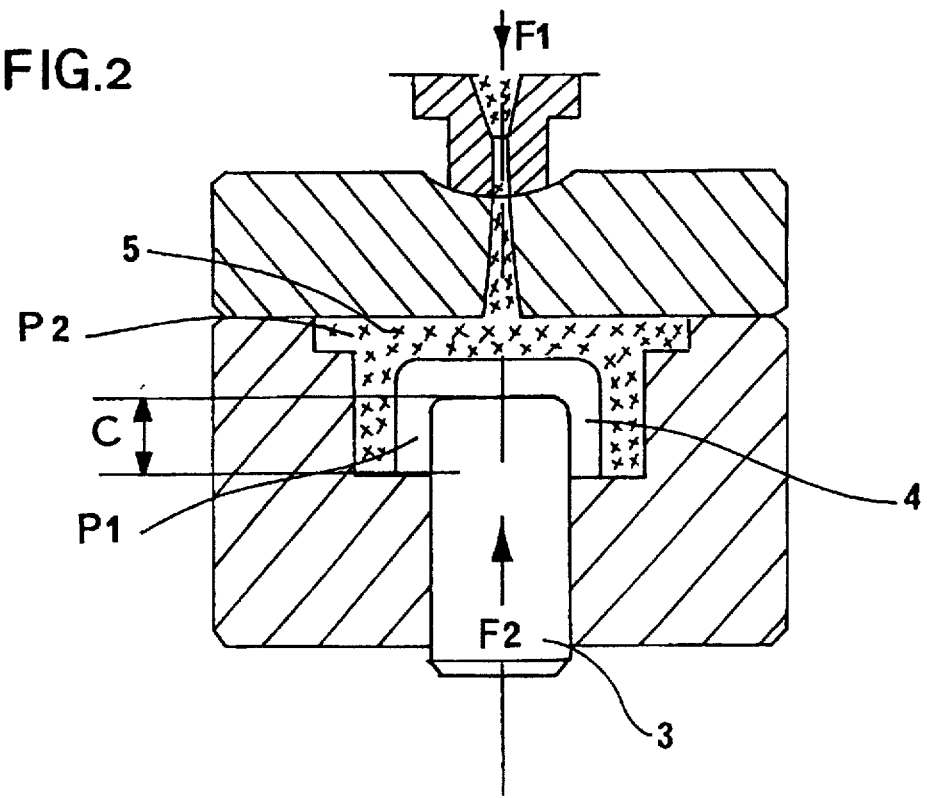
FIG. 2 shows the mold of FIG. 1 after controlled compression and forming of the part.
Figure 3:
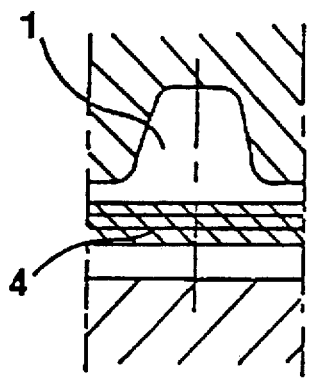
FIGS. 3 and 4 are cross-sectional views of a gear tooth mold (without the movable punch) respectively before and after compression.
Figure 4:
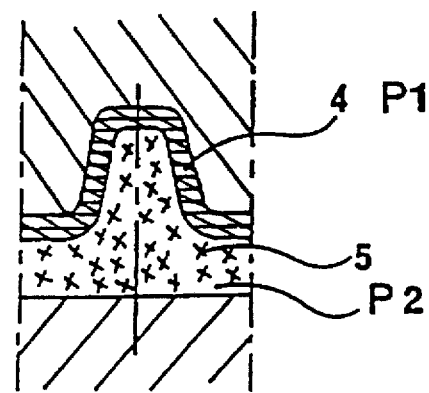

The step of compression which permits forming the part and which is subsequent to the steps of introduction of the plastic materials P1 and P2 into the mold can be effected in a variable and programmed manner. Thus, when said plastic materials are introduced within the mold cavity, the part is formed in the mold either by means of the injection pressure and solely by means of the latter as shown in FIG. 4, or by means of a punch 3 movable in the mold cavity as shown in FIG. 5, or by means both of the injection pressure and of the movable punch 3 as shown in FIG. 1. These three means to obtain a part having interesting mechanical properties permit covering a large number of uses. Thus, in certain cases, it is necessary that the blank constituted by a material highly resistant to flow and fatigue, which is to say generally a plastic material of high molecular weight and therefore being adapted to be subjected to a certain number of frictional strokes, be disposed at the surface of the part, as is the case in FIGS. 1, 3 and 5. On the other hand, in certain very rare cases, it is preferred that it be the injectable material that is disposed in the surface of the part. It can also be interesting to form the plastic material P2 in sandwich fashion between two blanks or between a blank and a reinforcing material or else to place in sandwich fashion between two blanks 4 or between the blank and the material P2 a reinforcement, or still again to use the blank 4 alone reinforced before its introduction into the mold or by means of a separate reinforcement element. The advantage of being able to use a movable punch within the mold cavity and if desired combining it with the injection pressure to form the part, as shown in FIGS. 1 and 2, is to be able to orient the molecular chains of the constituent polymer of the blank such that they will be parallel to the frictional surface at least in the region of the part located below or flush with this surface. This particular characteristic is especially obtained because the movable punch is displaced so that it comes into contact with the blank 4 so as to require the blank 4 to be oriented in a manner similar to that recited above. The molecular orientation following the practice introduces at the level of the mechanical properties an anisotropy which can be prejudicial to the dimensional stability of the final product. Injecting, or combining with a reinforced material, a blank at low temperature increases the orientation of this latter the more the flow temperature is low.

The process permits obtaining on the blank, for example the frictional portion of the part, small crystallites and a maximum orientation in the direction of force. Moreover, this orientation can be better controlled by the fact that use is made of a viscous pad 5 of the injected material P2. The action of the punch 3 on the blank 4 requires the blank and the injected plastic material P2 to assume the profile of the matrix constituted by the walls of the mold cavity and if desired the punch. Moreover, the fact of not reheating and bringing to the melting temperature only a portion of the blank as shown for example in FIGS. 1 and 2 permits better orienting the molecular chains in the cold portion. Moreover, these adjustment possibilities, particularly the fact that the advance of the piston can be controlled relative to the shear strength of the material of the viscous pad or relative to the speed of injection, permit obtaining a part with optimum internal tension.

To permit recovery of mechanical work, it is preferable to integrate a reinforcement either in the blank 4 or in the material P2 which is injected or not. Thus, in the case of FIG. 5, which shows the production of a gear tooth, the reinforced material is the material P2. On the contrary, in FIG. 1, it is the blank which is reinforced. The fact of reinforcing the blank permits obtaining a part whose surface, based on very high molecular weight material, has better resistance to wear, to fatigue with a high coefficient of friction and with mechanical performances which, thanks to the reinforcement, impart resistance to flow, the recovery of forces being due to the reinforcing material. This reinforcing material is integrated in or independent of the blank.

It is to be noted that the punch 3 movable in the mold cavity 1 is displaceable in translation in said cavity in the direction of the height of the blank 4. The pressure applied to the punch 3 to displace the punch to a final position permitting forming said materials is a function both of the composition of the blank 4 and if desired, when it is present, of the injected plastic material P2. The punch is maintained in final position for a period variable generally of several seconds so as to obtain homogeneous shrinkage and a good dimensional control of the final part without internal tension. Then, the formed part is extracted from the mold cavity by ejection means known per se. This mold cavity and this mold can be, as a function of the uses, of very variable shape, the mold being adapted to be formed in several parts, the injection point being located on one of the parts of the mold and the movable punch on one or the other part of the mold or, on the contrary, there can be used, according to FIG. 3, a mold comprising only one injection point without a movable punch, or again a mold comprising only a movable punch. Thanks to this process, it becomes easy to produce prosthetic articulations, particularly hip cotyles and tibial plates or mechanical parts.

An example of production of an abutment-bearing support is given hereafter according to FIGS. 1 and 2. The blank 4 of plastic material P1 is comprised by a very high molecular weight (6,000,000) machined polyethylene. It is brought to a temperature of 160° C. at its surface for a thickness 4a of 2 mm, the other thickness, of 4 mm, being at about 80° C. The injected material 5, which is plastic material P2, is very high molecular weight (3,500,000) polyethylene loaded with glass fibers. It is brought to 170° C. The blank 4 is disposed in the mold then there is very rapidly injected (1.5 second) a smaller volume of material than the volume of the impression. Then, the piston compresses the blank against the pad of injected material toward the side C. During this phase, the injection pressure is maintained below the residual pressure in the impression by the force P2 of the punch. Then, after cooling of the injection channel, the pressure of the piston will be programmed timewise for about 120 seconds.

The injection is controlled relative to the advance of the compression piston against the blank, which permits adjusting the amount of orientation of the material of the blank.

The portion on the injection side of the mold will be adjusted to 50°–60° C., that on the side compressed by the punch will be adjusted to 125° C. to 60° C. linearly over a time period of 240 seconds. The pressure exerted on the piston will also decrease from 120 kg/cm$^2$ to 50 kg/cm$^2$ during a cooling period of 240 seconds following an appropriate curve.

That avoids any stress in the molded part and permits adjusting the amorphous and crystalline phases.

It is to be noted that these numerical values are supplied only by way of example.

I claim:

1. A process for the production of a plastic material part with a wear-resistant surface having a predetermined nonplanar shape, comprising heating a blank of plastic material on a first side thereof opposite a second side on which second side it is desired to produce the wear-resistant surface, said plastic material comprising a polymer having molecular chains oriented parallel to said second side at least adjacent said second side, said heating of said first side bringing the temperature of said first side to adjacent the melting temperature of the plastic material while leaving the temperature of the second side substantially lower than the temperature of the first side, introducing said blank into a mold cavity, and subjecting said blank to elevated pressure in said mold cavity with a surface of said mold cavity in contact with said second side having a nonplanar shape complementary to said predetermined nonplanar shape, thereby to impart to said second side said predetermined shape while said second side is at said substantially lower temperature.

2. A process as claimed in claim 1, wherein said surface of said mold cavity is produced by extending a retractable punch into the mold cavity in contact with the blank.

3. A process as claimed in claim 1, wherein said surface of said mold cavity is stationary and said blank is pressed into contact with said stationary surface of the mold cavity by pressure of a liquid.

4. A process as claimed in claim 3, wherein said liquid is a plastic which hardens into a monolithic piece with said blank.

5. A process as claimed in claim 1, wherein said blank is reinforced with a reinforcing material prior to introduction into the mold cavity.

6. A process as claimed in claim 5, wherein said reinforcing material is a fabric.

7. A process as claimed in claim 1, wherein said blank is of high molecular weight polyethylene.

8. A process according to claim 1, wherein said part is an osteo implant.

9. A process as claimed in claim 8, wherein said implant is a cotyle.

* * * * *